United States Patent
Kim et al.

(10) Patent No.: US 10,213,515 B2
(45) Date of Patent: Feb. 26, 2019

(54) GLYCOPEPTIDE FOR CONTRAST AGENT TARGETING CANCER CELLS AND CONTRAST AGENT KIT CONTAINING THE SAME

(71) Applicant: KOREA INSTITUTE OF SCIENCE AND TECHNOLOGY, Seoul (KR)

(72) Inventors: Kwangmeyung Kim, Seoul (KR); Ju Hee Ryu, Seoul (KR); Ick Chan Kwon, Seoul (KR); Man Kyu Shim, Seoul (KR); Hong Yeol Yoon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 49 days.

(21) Appl. No.: 15/169,493

(22) Filed: May 31, 2016

(65) Prior Publication Data

US 2017/0216460 A1     Aug. 3, 2017

(30) Foreign Application Priority Data

Jun. 9, 2015   (KR) .................. 10-2015-0081418

(51) Int. Cl.
| | | |
|---|---|---|
| *A61K 51/00* | (2006.01) | |
| *A61M 36/14* | (2006.01) | |
| *A61K 49/00* | (2006.01) | |
| *C07K 9/00* | (2006.01) | |
| *G01N 33/574* | (2006.01) | |
| *G01N 33/58* | (2006.01) | |
| *C07K 5/11* | (2006.01) | |
| *C07K 5/107* | (2006.01) | |
| *A61K 47/54* | (2017.01) | |

(52) U.S. Cl.
CPC ........ *A61K 49/0056* (2013.01); *A61K 47/555* (2017.08); *A61K 49/0032* (2013.01); *A61K 49/0052* (2013.01); *C07K 5/1016* (2013.01); *C07K 5/1019* (2013.01); *C07K 9/001* (2013.01); *G01N 33/57496* (2013.01); *G01N 33/581* (2013.01); *G01N 2333/96466* (2013.01)

(58) Field of Classification Search
CPC ............. A61K 49/00; A61K 49/0056; A61K 49/0032; A61K 2121/00; A61K 2123/00; A61K 38/00; A61K 49/0052; G01N 33/57496; G01N 33/581; G01N 2333/96466; C07K 9/001; C07K 5/1019; C07K 5/1016; C07K 47/555

USPC ......... 424/1.11, 1.65, 1.69, 1.81, 1.85, 1.89, 424/9.1, 9.2, 90.3, 9.4, 9.5, 9.6, 1.73, 9.3; 514/1, 1.1, 19.2, 19.3, 19.4, 19.5, 19.6; 530/300

See application file for complete search history.

(56) References Cited

PUBLICATIONS

Dal Corso et al, Chem. Eur. J., vol. 21, pp. 6921-6929. (Year: 2015).*
Maschauer et al, Molecular Pharmaceutics, vol. 11, No. 2, pp. 505-515. (Year: 2014).*
Chang et al, A Strategy for the Selective Imaging of Glycans Using Caged Metabolic Precursors, Journal of the American Chemical Society , Jun. 22, 2010, pp. 9516-9518, vol. 132, JACS communications.
Sinha et al. Localization of a Biotinylated Cathepsin B Oligonucleotide Probe in Human Prostate Including Invasive Cells and Invasive Edges by in Situ Hybridization, The Anatomical record, 1993, pp. 233-40, vol. 235.
Murnane et al. Stage-specific Increases in Cathepsin B Messenger RNA Content in Human Colorectal Carcinoma1 Cancer Research ,Feb. 15, 1991, pp. 1137-1142, vol. 51.
Rempel et al. Cathepsin B Expression and Localization in Glioma Progression and Invasion,Cancer Research, Dec. 1, 1994, pp. 6027-6031, vol. 54, American Association for Cancer Research.
Frohlich et al., Activity, Expression, and Transcription Rate of the Cathepsins B, D, H, and L in Cutaneous Malignant Melanoma, Cathepsins in Malignant Melanoma, Mar. 1, 2001, pp. 972-982, vol. 91, No. 5, Cancer.
Roshy et al., Pericellular cathepsin B and malignant progression, Cancer and Metastasis Reviews, 2003, pp. 271-286, vol. 22.
B.F.Sloane et al. Cathepsin B and tumor proteolysis: contribution of the tumor microenvironment, Seminars in Cancer Biology 2005, pp. 149-157, vol. 15, Elsevier.
Sloane et al. Cathepsin B: Association with plasma membrane in metastatic tumors, Proceedings of the National Academy of Sciences , Apr. 1986, pp. 2483-2487, vol. 83, Cell Biology.

* cited by examiner

*Primary Examiner* — D. L. Jones
(74) *Attorney, Agent, or Firm* — Goldilocks Zone IP Law

(57) ABSTRACT

The present disclosure relates to a glycopeptide targeting cancer cells and a contrast agent kit containing the same. The glycopeptide is one wherein an azide reporting monosaccharide is bound to a substrate peptide. As the substrate peptide is specifically cleaved by cathepsin B in cancer cells, an azide reporting monosaccharide is expressed onto the cell surface via metabolic glycoengineering, thereby providing a target for action as a contrast agent. Accordingly, because the azide is exposed to the cell surface only by cathepsin B, as it is specifically expressed in cancer cells, in particular in metastatic cancer cells, while it is limitedly expressed in normal cells and is hardly excreted out the cells, the cancer cells can be selectively imaged by an azide-specific contrast agent.

9 Claims, 17 Drawing Sheets
Specification includes a Sequence Listing.

1. Non-treated
2. RR-S-Ac$_3$ManNAz
3. RR-S-Ac$_3$ManNAz + inh
4. Ac$_3$ManNAz
5. Ac$_3$ManNAz + inh 1. Saline
2. RR-S-Ac$_3$ManNAz + inh
3. RR-S-Ac$_3$ManNAz

GLYCOPEPTIDE FOR CONTRAST AGENT TARGETING CANCER CELLS AND CONTRAST AGENT KIT CONTAINING THE SAME

CROSS-REFERENCE TO RELATED APPLICATIONS

This application claims, under 35 U.S.C. § 119, the priority of Korean Patent Application No. 10-2015-0081418, filed on Jun. 9, 2015 in the Korean Intellectual Property Office, the disclosure of which is incorporated herein by reference in its entirety.

TECHNICAL FIELD

The present disclosure relates to a glycopeptide for a contrast agent targeting cancer cells, a contrast agent kit containing the glycopeptide and a contrast method targeting cancer cells using the contrast agent kit.

BACKGROUND

Cancer refers to a group of diseases wherein a mass or tumor of undifferentiated cells that grow unregulatedly and unlimitedly is formed in tissues. By infiltrating into and destroying nearby normal tissues or organs and metastasizing from the primary site a new site in other tissues or organs, it can ultimately take the life of an organism.

For decades, a lot of nanomaterials and drugs have been attempted as contrast agents targeting cancer cells or targeted drug delivery systems. Among them, the 'active targeting system' based on the genetic information of cancer cells has provided an insight for remarkable cancer cell targeting efficiency. However, the currently achievable cancer cell targeting efficiency is still limited and there are many obstacles in improving the targeting efficiency. In particular, the current active targeting strategy based on genetic information has intrinsic limitations because the receptors present on the cancer cell surface are restricted in their type or amount. In addition, the heterogeneity of cancer cells makes the situation even more complicated due to various mutations of the cancer cells that express receptors of different types and amounts. This heterogeneity is observed even within the tumor cells of the same tissue. As a result, many nanomaterials and drugs targeting the receptors present on the cancer cell surface can be easily saturated with the receptors and this leads to decreased efficiency of targeted imaging or targeted drug delivery.

Therefore, if targetable chemical groups can be introduced into cancer tissues containing heterogeneous cancer cells, they can be used as artificial active targeting sites for delivery of nanomaterials. This is expected to be a solution for overcoming the heterogeneity of cancer cells.

Recently, Bertozzi et al. developed a metabolite cleaved by the prostate-specific antigen protease and demonstrated the introduction of azide groups into cancer cells in vitro. However, they did not present an in-vivo experiment result (non-patent document 1).

Cathepsin B is one of cysteine proteases. Increased amount of its mRNA as compared to normal cells is reported in human-derived prostate cancer cells (non-patent document 2), colorectal cancer cells (non-patent document 3), glioma cells (non-patent document 4) and melanoma cells (non-patent document 5). Also, increased expression and activity of the enzyme is reported in breast cancer, colon cancer, esophageal cancer, stomach cancer, lung cancer, uterine cancer and thyroid cancer (non-patent document 6). In particular, increased expression of cathepsin B is reported in metastatic cancer (non-patent documents 7 and 8).

REFERENCES OF THE RELATED ART

Non-Patent Documents (Non-patent document 1) P. V. Chang, D. H. Dube, E. M. Sletten, C. R. Bertozzi, *Journal of the American Chemical Society* 2010, 132, 9516-9518.
(Non-patent document 2) Sinha, A. A.; Gleason, D. F.; Deleon, O. F.; Wilson, M. J.; Sloane, B. F. *Anat Rec* 1993, 235, 233-40.
(Non-patent document 3) Murnane, M. J.; Sheahan, K.; Ozdemirli, M.; Shuja, S. *Cancer Res* 1991, 51, 1137-42.
(Non-patent document 4) Rempel, S. A.; Rosenblum, M. L.; Mikkelsen, T.; Yan, P. S., Ellis, K. D.; Golembieski, W. A.; Sameni, M.; Rozhin, J.; Ziegler, G.; Sloane, B. F. *Cancer Res* 1994, 54, 6027-31.
(Non-patent document 5) Frohlich, E.; Schlagenhauff, B.; Mohrle, M.; Weber, E.; Klessen, C.; Rassner, G. *Cancer* 2001, 91, 972-82.
(Non-patent document 6) Roshy, S.; Sloane, B. F.; Moin, K. *Cancer Metastasis Rev* 2003, 22, 271-86.
(Non-patent document 7) Sloane, B. F.; Yan, S.; Podgorski, I.; Linebaugh, B. E.; Cher, M. L.; Mai, J.; Cavallo-Medved, D.; Sameni, M.; Dosescu, J.; Moin, K. *Seminars in Cancer Biology* 2005, 15, 149-157.
(Non-patent document 8) Sloane, B. F.; Rozhin, J.; Johnson, K.; Taylor, H.; Crissman, J. D.; Honn, K. V. *Proceedings of the National Academy of Sciences* 1986, 83, 2483-2487.

SUMMARY

The present disclosure is directed to providing a glycopeptide for a contrast agent targeting cancer cells, whose expression is limited in normal cells and which is capable of specifically targeting various cancer cells and cancer tissues. The present disclosure is also directed to providing a glycopeptide for a contrast agent targeting cancer cells, which is useful in predicting or diagnosing metastatic cancer.

The present disclosure is also directed to providing a contrast agent kit targeting cancer cells, which contains the glycopeptide for a contrast agent targeting cancer cells.

The present disclosure is also directed to providing a contrast method targeting cancer cells using the glycopeptide for a contrast agent targeting cancer cells.

In an aspect, the present disclosure provides a glycopeptide for a contrast agent targeting cancer cells, wherein an azide reporting monosaccharide is bound to a substrate peptide specifically degraded by cathepsin B.

In another aspect, the present disclosure provides a contrast agent kit targeting cancer cells, which contains the glycopeptide for a contrast agent targeting cancer cells and a cyclooctyne-labeling fluorescent material.

In another aspect, the present disclosure provides a contrast method targeting cancer cells, which includes: administering the glycopeptide for a contrast agent targeting cancer cells; and subsequently administering a cyclooctyne-labeling fluorescent material.

The present disclosure relates to a glycopeptide targeting cancer cells and a contrast agent kit containing the same. The glycopeptide is one wherein an azide reporting monosaccharide is bound to a substrate peptide. As the substrate peptide is specifically cleaved by cathepsin B in cancer cells, an azide reporting monosaccharide is expressed onto the cell surface via metabolic glycoengineering, thereby providing a target for action as a contrast agent. Accordingly, because the azide is exposed to the cell surface only by cathepsin B, as it is specifically expressed in cancer cells, in particular in metastatic cancer cells, while it is limitedly expressed in normal cells and is hardly excreted out the cells, the cancer cells can be selectively imaged by an azide-specific contrast agent.

DETAILED DESCRIPTION OF EMBODIMENTS

Figure 1A:
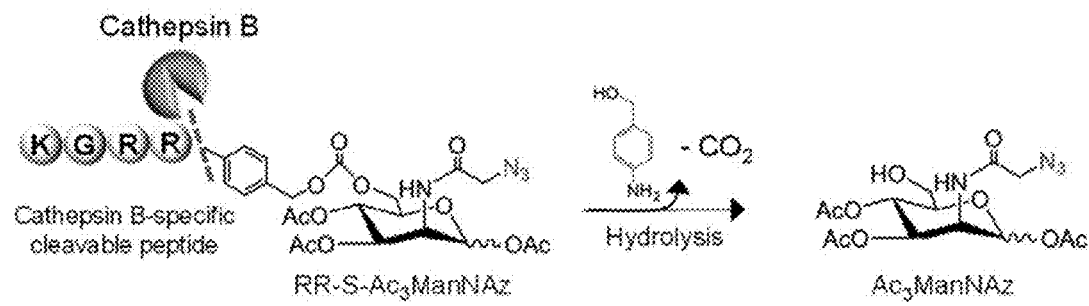
FIG. 1A schematically shows that a bond between a cathepsin B-specific substrate peptide and a linker (S) is cleaved by cathepsin B (dotted line) and the linker (S), the substrate peptide (KGRR) and Ac$_3$ManAz are released as a result.

Hereinafter, the present disclosure is described in more detail.

A glycopeptide for a contrast agent targeting cancer cells of the present disclosure is one wherein an azide reporting monosaccharide is bound to a substrate peptide specifically degraded by cathepsin B.

The glycopeptide for a contrast agent targeting cancer cells is a substrate peptide which has an amino acid sequence specifically degraded by cathepsin B.

Because cathepsin B is specifically expressed in cancer cells, in particular in metastatic cancer cells, whereas it is limitedly expressed in normal cells, it can be used to detect metastatic cancer. In addition, because it is hardly excreted extracellularly, the risk of a false positive error of detecting normal cells or normal tissue as cancer cells or cancer tissue is very low. In contrast, a prostate-specific antigen (PSA) protease used by Bertozzi et al., for example, is expressed only in prostate cancer, and thus it is not suitable for detection of cancers other than prostate cancer and it is difficult to detect metastatic cancer. In particular, because the enzyme is excreted extracellularly, there is a risk of a false positive error of falsely detecting normal cells or normal tissue.

The substrate peptide may be a peptide composed of 4-30 amino acids containing an amino acid sequence of SEQ ID NO 1.

The substrate peptide may be a peptide composed of 4 amino acids of lysine-glycine-arginine-arginine (KGRR) of SEQ ID NO 1 or a peptide composed of 5-30 amino acids wherein 1-26 amino acid(s) is (are) further bound to the N-terminal lysine of the peptide of SEQ ID NO 1. Cathepsin B recognizes the C-terminal arginine-arginine (RR) sequence of the peptide of SEQ ID NO 1 and cleaves the C-terminal. Accordingly, the amino acid(s) further bound to the N-terminal is(are) not limited in kind or sequence. But, if the number of the amino acids of the substrate peptide exceeds 30, glycoengineering may be restricted.

Specifically, the amino group of the N-terminal amino acid of the substrate peptide may be acetylated.

During the preparation procedure of the glycopeptide for a contrast agent targeting cancer cells, an amine protecting group may be used to protect the nitrogen atom of the amine group of the substrate peptide. The amine protecting group may be any one known in the art without limitation. For example, a methyloxycarbonyl group, a benzyloxycarbonyl group, a p-methoxybenzyloxycarbonyl group, a t-butyloxycarbonyl (Boc) group, a 9-fluorenylmethyloxycarbonyl (FMOC) group, an allyloxycarbonyl (Alloc) group, a benzoyl (Bz) group, a benzyl (Bn) group, a p-methoxybenzyl (PMB) group, a 3,4-dimethoxybenzyl (DMPM) group, a p-methoxyphenyl (PMP) group, a tosyl (Ts) group, a trimethylsilylethyloxycarbonyl (Teoc) group, a benzhydryl group, a triphenylmethyl (trityl) group, a (4-methoxyphenyl) diphenylmethyl (Mmt) group, a dimethoxytrityl (DMT) group, a diphenylphosphino group, etc. may be used.

The azide reporting monosaccharide (or azide reporter) expresses azide onto the surface of cancer cells via glycoengineering and may be one or more selected from N-azidoalkyl-D-mannosamine, N-azidoalkyl-D-galactosamine and N-azidoalkyl-D-glucosamine. In the azide reporting monosaccharide, the alkyl group may be a $C_1$-$C_3$ alkyl group, specifically an acetyl group.

The substrate peptide and the azide reporting monosaccharide may be bound directly or a linker may be bound between them. When bound to the substrate peptide, the linker maintains a stable bonding state with the azide reporting monosaccharide under in-vivo physiological environment. But, when the C-terminal of the substrate peptide is cleaved by cathepsin B, the azide reporting monosaccharide is separated from the linker and released intact. Accordingly, the linker does not affect the expression of azide onto the cancer cell surface via glycoengineering.

One end of the linker may be bound to the C-terminal of the substrate peptide and the other end may be bound to the C-6 hydroxyl group of the azide reporting monosaccharide. For example, the linker may be selected from 6-maleimidocaproyl (MC), maleimidopropanoyl (MP), valine-citrulline (val-cit), alanine-phenylalanine (ala-phe), p-aminobenzyloxycarbonyl (PAB), N-succinimidyl 4-(2-pyridylthio) pentanoate (SPP), N-succinimidyl 4-(N-maleimidomethyl) cyclohexane-1 carboxylate (SMCC) and N-succinimidyl (4-iodo-acetyl)aminobenzoate (SIAB).

Therefore, when the glycopeptide for a contrast agent targeting cancer cells is administered into the body, glycoengineering does not occur in normal cells or normal tissue because the substrate peptide is not cleaved and, accordingly, azide is not expressed onto the surface of normal cells. In contrast, in cancer cells or cancer tissue, cleavage occurs between the substrate peptide and the azide reporting monosaccharide, between the substrate peptide and the linker or between the linker and the azide reporting monosaccharide by cathepsin B expressed in the cancer cells. As a result, the azide reporting monosaccharide is exposed onto the cancer cell surface via glycoengineering and azide is expressed.

Because the azide is expressed selectively on the cancer cell surface, cancer cells can be detected selectively by administering a cyclooctyne-labeling fluorescent material which binds specifically to the azide into the body. The glycopeptide for a contrast agent targeting cancer cells is particularly suitable to detect metastatic cancer.

FIG. 1 schematically shows that $Ac_3ManAz$ is released onto the surface of cancer cells from RR-S-$Ac_3$ManAz, a glycopeptide for a contrast agent targeting cancer cells according to an exemplary embodiment of the present disclosure, by cathepsin B.

FIG. 1A schematically shows that a bond between a cathepsin B-specific substrate peptide and a linker (S) is cleaved by cathepsin B (dotted line) and the linker (S), the substrate peptide (KGRR) and $Ac_3$ManAz are released as a result.

Figure 1B:
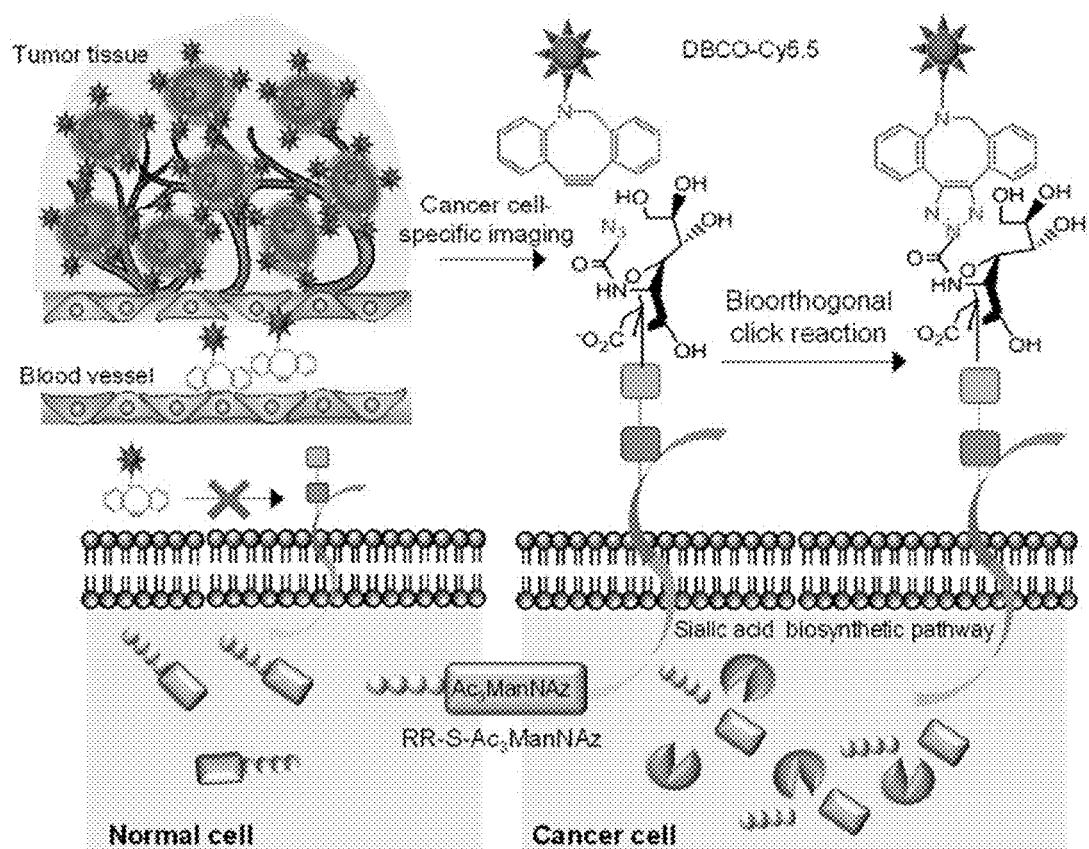
FIG. 1B schematically shows that Ac$_3$ManAz is metabolized in cancer cells via glycoengineering, expressed onto the cancer cell surface and labeled by a cyclooctyne-labeling fluorescent material DBCO-Cy5.5 via a bioorthogonal click reaction and that RR-S-Ac$_3$ManAz expresses azide to cell surface glycan in cancer cells via sialic acid biosynthesis whereas it does not in normal cells.

FIG. 1B schematically shows that $Ac_3$ManAz is metabolized in cancer cells via glycoengineering, expressed onto the cancer cell surface and labeled by a cyclooctyne-labeling fluorescent material DBCO-Cy5.5 via a bioorthogonal click reaction and that RR-S-$Ac_3$ManAz expresses azide to cell surface glycan in cancer cells via sialic acid biosynthesis whereas it does not in normal cells.

In the cyclooctyne-labeling fluorescent material, the cyclooctyne may be one or more compound selected from a group consisting of dibenzylcyclooctyne (DBCO), difluorocyclooctyne (DIFO), bicyclononyne (BCN), dibenzoazacyclooctyne (DIBAC), dibenzocyclooctynol (DIBO) and azadibenzocyclooctyne (ADIBO).

The fluorescent material may be, for example, cyanine, allophycocyanin, fluorescein, tetramethylrhodamine, BODIPY, Alexa, etc. Among these fluorescent materials, cyanine dyes are preferred because they emit and absorb near-infrared light and thus exhibit low interference in cells, blood, biological tissues, etc. Specifically, Cy5.5 may be used.

The cyclooctyne-labeling near-infrared fluorescent material allows for in-vivo imaging of tissues of autoimmune disease patients by irradiating near-infrared light and various types of molecular imaging are possible when radioisotopes, quantum dots and MRI contrast agents are introduced together.

Hereinafter, the present disclosure will be described in more detail through examples. However, the following examples are for illustrative purposes only and not intended to limit the scope of this disclosure.

Example 1: Synthesis of RR-S-$Ac_3$ManNAz

4-Aminobenzyl alcohol (227 mg, 1.8 mmol) was added to a solution of Ac—K(Alloc)GR(Alloc)$_2$R(Alloc)$_2$-OH (901 mg, 0.92 mmol) and N-ethoxycarbonyl-2-ethoxy-1,2-dihydroquinoline (EEDQ; 455 mg, 1.8 mmol) in anhydrous dimethylformamide (DMF; 25 mL). The resulting solution was stirred at room temperature for 24 hours under argon gas. After removing DMF from the solution under reduced pressure, the product was precipitated in diethyl ether and washed 3 times with diethyl ether (20 mL) to yield Ac—K (Alloc)GR(Alloc)$_2$R(Alloc)$_2$-PABOH [mass (ESI-MS, MW 1083.15): m/z 1084.3 [M+H]$^+$].

Ac—K(Alloc)GR(Alloc)$_2$R(Alloc)$_2$-PABOH (145 mg, 0.13 mmol) and 4-nitrophenyl chloroformate (4-NPC, 32.4 mg, 0.16 mmol) were dissolved in anhydrous dichloromethane (DOM; 3.5 mL) under argon gas and 2,6-lutidine (47 μL, 0.40 mmol) was added. The resulting solution was stirred for 6 hours while further adding DMF (1.5 mL), 2,6-lutidine (74 μL, 0.64 mmol) and 4-nitrophenyl chloroformate (27 mg, 0.13 mmol). The reaction solution was extracted with ethyl acetate and then purified by preparative high-performance liquid chromatography (HPLC) to yield Ac—K(Alloc)GR (Alloc)$_2$R(Alloc)$_2$-PABC [mass (ESI-MS, MW 1248.25): m/z 1249.6 [M+H]$^+$].

$Ac_3$ManNAz (21.5 mg, 0.055 mmol) and N,N-dimethylpyridin-4-amine (DMAP; 12.3 mg, 0.1 mmol) were added to a solution of Ac—K(Alloc)GR (Alloc)$_2$R(Alloc)$_2$-PABC (63 mg, 0.05 mmol) in anhydrous DCM (5 mL) and stirred overnight at room temperature under argon gas. The volatile components were removed under reduced pressure and the residue was purified by preparative HPLC to yield Ac—K (Alloc)GR(Alloc)$_2$R(Alloc)$_2$-PABC-$Ac_3$ManNAz [mass (ESI-MS, MW 1497.48): m/z 1498.1 [M+H]$^+$].

In order to remove the amine protecting group from the peptide, Ac—K(Alloc)GR(Alloc)$_2$R(Alloc)$_2$-PABC-$Ac_3$ManNAz (34.7 mg, 0.023 mmol), tetrakis(triphenylphosphine)palladium (13.4 mg, 0.0116 mmol), tributyltin hydride (106 μL, 0.40 mmol) and acetic acid (26.6 μL, 0.464 mmol) were dissolved in anhydrous DMF (3 mL) and stirred at room temperature for 1 hour under argon gas. The residue was purified by preparative HPLC to yield RR-S-Ac$_3$ManNAz [mass (ESI-MS, MW 1077.1): m/z 1078.1 [M+H]$^+$].

Figure 2A:
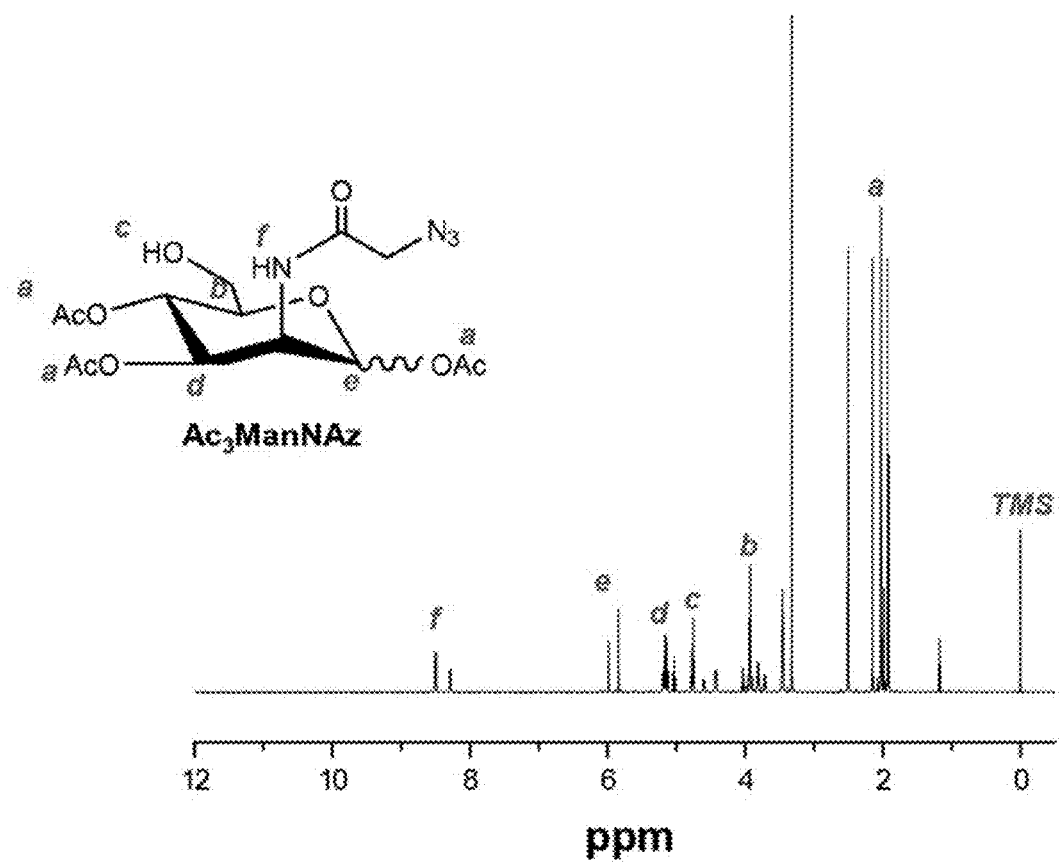
FIG. 2A shows the 600 MHz $^1$H-NMR spectrum of Ac$_3$ManNAz of Example 1.
Figure 2B:
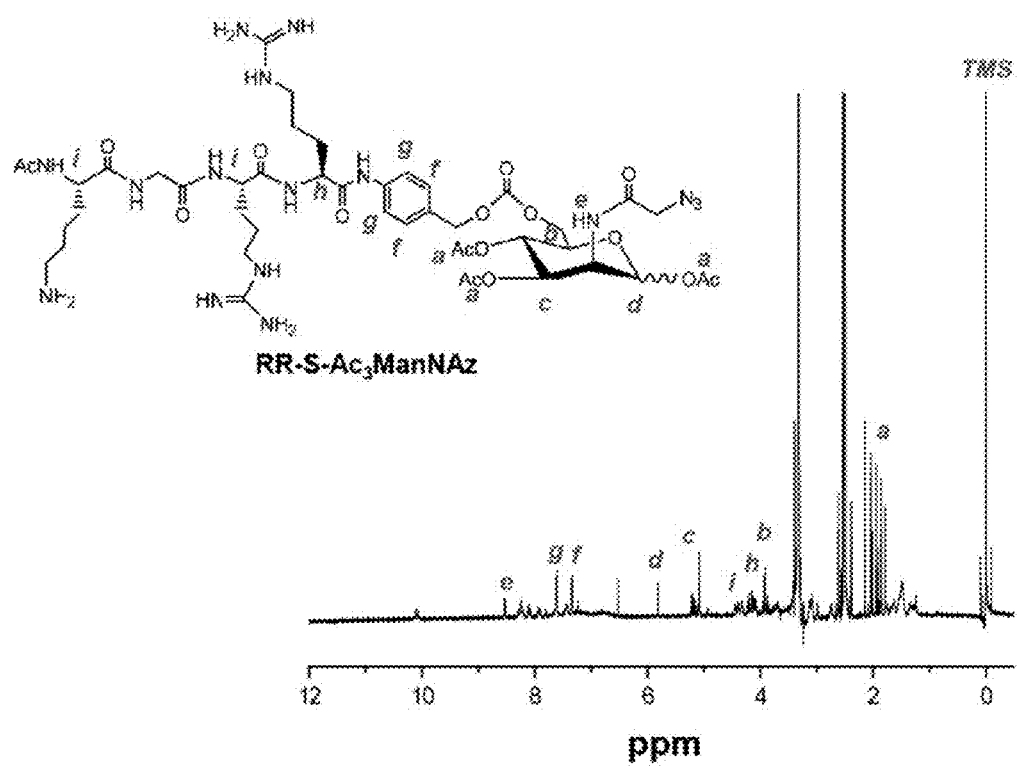
FIG. 2B shows the 600 MHz $^1$H-NMR spectrum of RR-S-Ac$_3$ManNAz of Example 1.

To confirm the chemical structures of Ac$_3$ManNAz and RR-S-Ac$_3$ManNAz, they were dissolved respectively in DMSO-d$_6$ and characteristic peaks were measured by 600 MHz $^1$H-NMR (DD2 600 MHz FT NMR, Agilent Technologies, USA). The result is shown in FIGS. 2A and 2B. The characteristic $^1$H-NMR peaks of Ac$_3$ManNAz and RR-S-Ac$_3$ManNAz are shown in FIG. 2A and FIG. 2B, respectively.

Example 2: Time-Dependent In Vitro Release of Ac$_3$ManNAz

To observe the release of Ac$_3$ManNAz from RR-S-Ac$_3$ManNAz in the presence or absence of cathepsin B, 500 µM RR-S-Ac$_3$ManNAz in a 25 mM 2-(N-morpholine)-ethanesulfonic acid reaction buffer was incubated with or without cathepsin B (50 µg/mL) for 0, 3, 6 and 12 hours at 37° C. The samples were analyzed by reversed-phase HPLC (Agilent Technologies 1200 series, Agilent Technologies, USA) using a C18 analytical column (100:0 H$_2$O:acetonitrile+0.1% TFA to 60:40 H$_2$O:acetonitrile+0.1% TFA for 60 minutes). Detection was made at 210 nm. The result is shown in FIG. 3A and FIG. 3B.

Figure 3A:
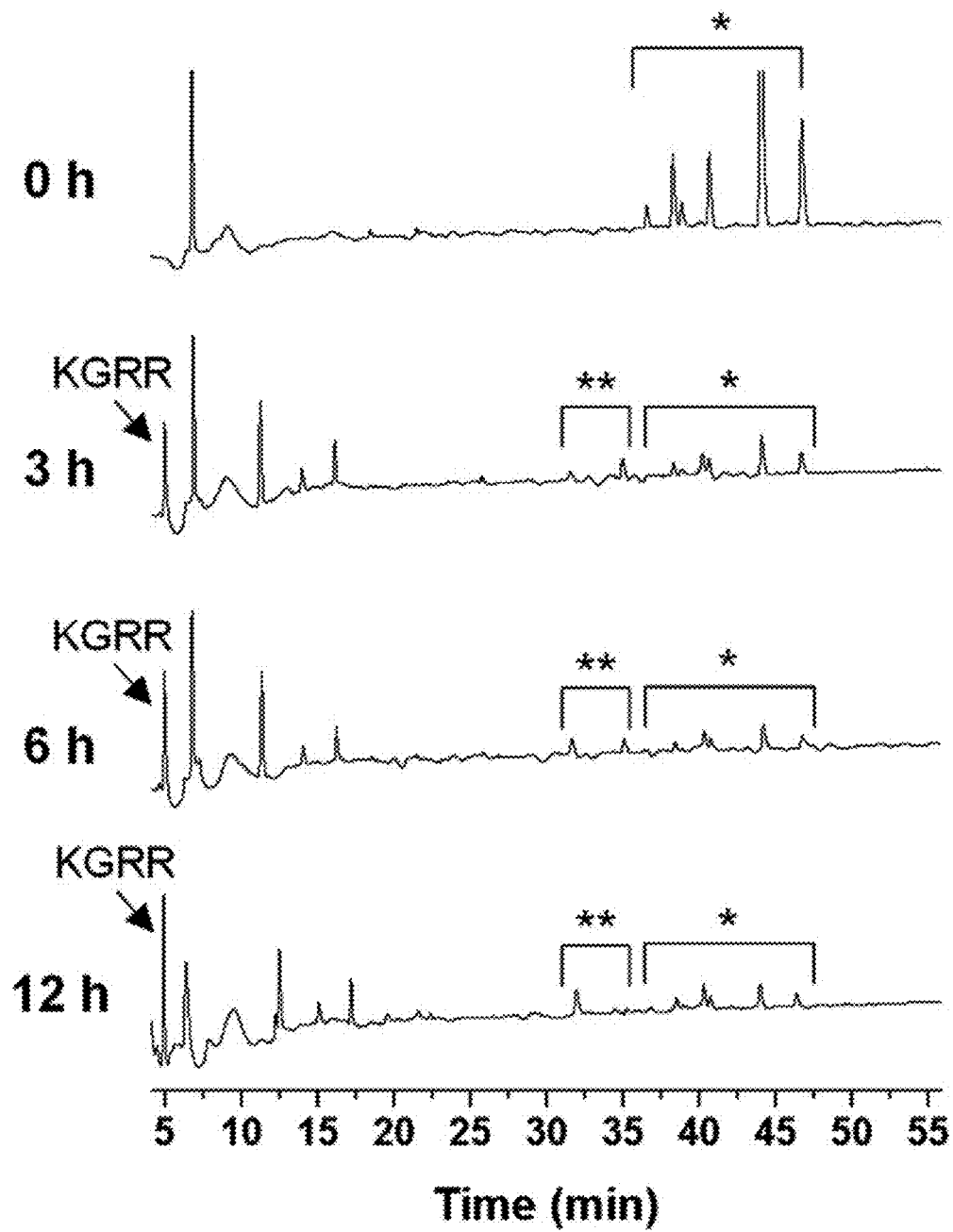
FIG. 3A shows the HPLC spectra of RR-S-Ac$_3$ManNAz (indicated by *) and Ac$_3$ManNAz (indicated by **) in a reaction solution containing cathepsin B in Example 2 with time.
Figure 3B:
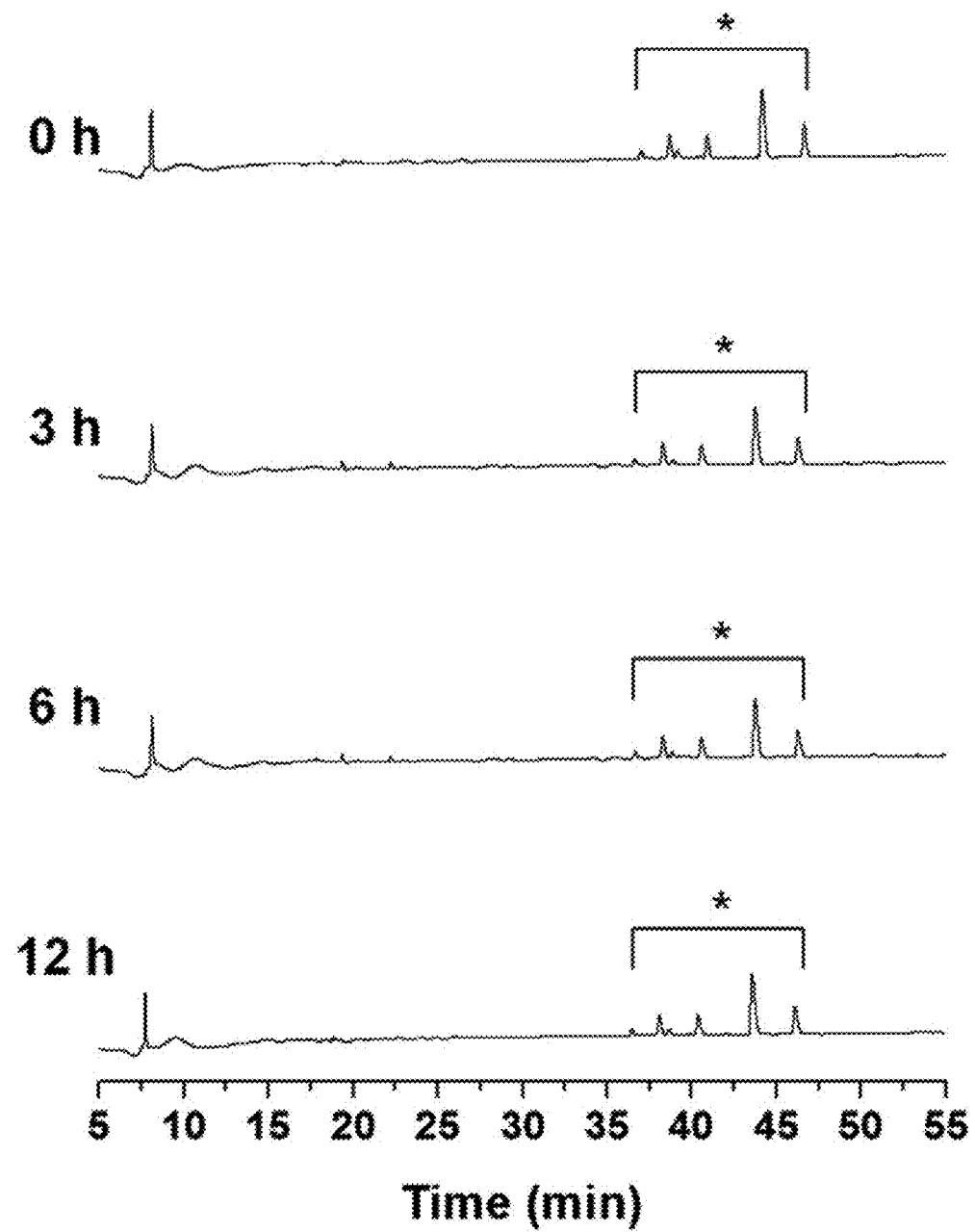
FIG. 3B shows the HPLC spectra of RR-S-Ac$_3$ManNAz (indicated by *) in a reaction solution without cathepsin B in Example 2 with time.

FIGS. 3A and 3B show the HPLC peaks of RR-S-Ac$_3$ManNAz (indicated by *) and Ac$_3$ManNAz (indicated by **) in a reaction solution containing cathepsin B (a) and in in a reaction solution not containing cathepsin B (b) with time.

When RR-S-Ac$_3$ManNAz was incubated with cathepsin B, the KGRR substrate peptide and Ac$_3$ManNAz were released from RR-S-Ac$_3$ManNAz in a time-dependent manner (FIG. 3A). However, in the reaction solution not containing cathepsin B, the release of Ac$_3$ManNAz could not be observed until 12 hours (FIG. 3B).

Figure 3C:
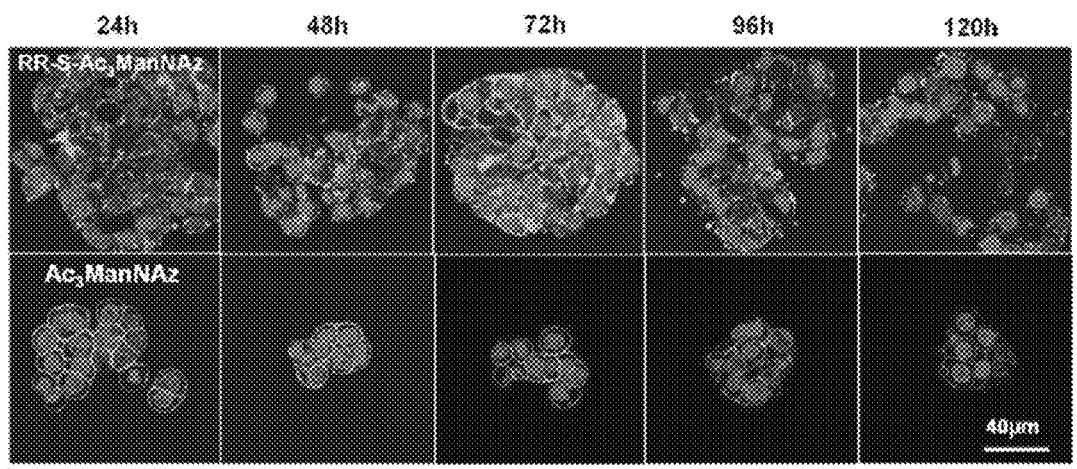
FIG. 3C shows the time-dependent fluorescence images of an azide reporting monosaccharide on the surface of HT-29 cells in vitro in Example 2. The images are confocal microscopic images of HT-29 cells treated with RR-S-Ac$_3$ManNAz or Ac$_3$ManNAz and then with DBCO-Cy5.

FIG. 3C shows the time-dependent fluorescence images of an azide reporting monosaccharide on the surface of HT-29 cells in vitro. The images are confocal microscopic images of HT-29 cells treated with RR-S-Ac$_3$ManNAz (5 µM) or Ac$_3$ManNAz (5 µM) and then with DBCO-Cy5 (200 nM). Red=DBCO-Cy5 channel; blue=DAPI channel.

In order to confirm the expression of azide on the cancer cell surface, 2.0×10$^4$ human-derived colon cancer HT-29 cells were seeded into 35-mm cover glass bottom dishes and incubated with media containing RR-S-Ac$_3$ManNAz (5 µM) or Ac$_3$ManNAz (5 µM) for 24 hours, 48 hours, 72 hours, 96 hours and 120 hours at 37° C. in a carbon dioxide incubator.

To visualize the expression of the azide reporting monosaccharide on the surface of the HT-29 cells, the cells were incubated with 5 µM DBCO-Cy5 for 2 hours at 37° C. and then washed with Dulbecco's phosphate-buffered saline (DPBS). After treating with a fixation solution for 15 minutes, the nuclei of the cells were stained by treating with a 4,6-diamidino-2-phenylindole (DAPI) solution for 10 minutes. Then, the fluorescence by DBCO-Cy5 bound to the expressed azide was observed using a confocal microscope.

Both the RR-S-Ac$_3$ManNAz- and Ac$_3$ManNAz-treated HT-29 cells showed strong fluorescence signals on the cell surface at 24 hours. For RR-S-Ac$_3$ManNAz, the fluorescence intensity increased gradually up to 72 hours and then decreased. It is because the HT-29 cells express cathepsin B and, thus, Ac$_3$ManNAz is released continuously as the substrate peptide is cleaved from RR-S-Ac$_3$ManNAz. In contrast, the Ac$_3$ManNAz-treated HT-29 cells showed gradually decreased azide expression after 48 hours.

Figure 4A:
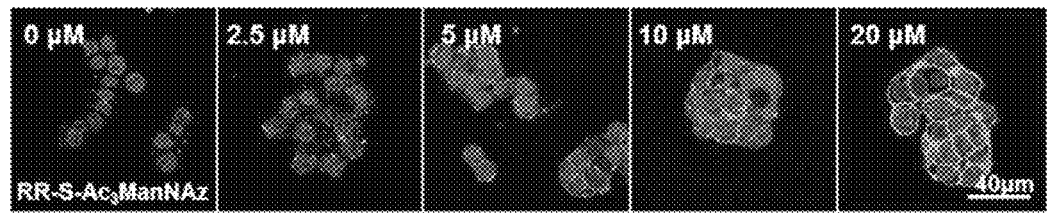
FIG. 4A shows confocal microscopic images showing fluorescence intensity depending on the concentration of RR-S-Ac$_3$ManNAz in Example 2.
Figure 4B:
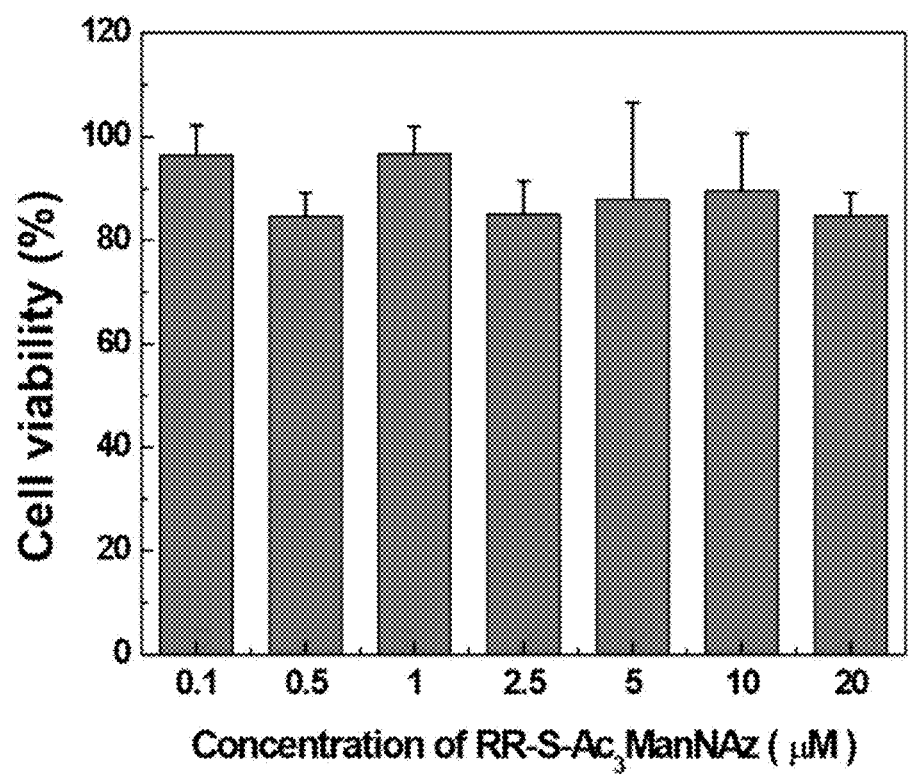
FIG. 4B shows cytotoxicity depending on the concentration of RR-S-Ac$_3$ManNAz in Example 2.

FIG. 4A shows confocal microscopic images showing fluorescence intensity depending on the concentration of RR-S-Ac$_3$ManNAz and FIG. 4B shows cytotoxicity depending on the concentration of RR-S-Ac$_3$ManNAz.

As can be seen from FIG. 4A and FIG. 4B, the amount of the azide reporting monosaccharide expressed onto the surface increased with the concentration of RR-S-Ac$_3$ManNAz in a concentration-dependent manner and cytotoxicity was not observed up to 20 µM. Based on this result, the concentration of RR-S-Ac$_3$ManNAz was fixed at 5 µM and the expression of the azide reporting monosaccharide was determined after incubation for 72 hours in the following experiments.

Example 3: Evaluation of Azide Expression Efficiency in Cancer Cells by RR-S-Ac$_3$ManNAz Using Cathepsin B Inhibitor 2.0×10$^4$ HT-29 cells were seeded into 35-mm cover glass bottom dishes, incubated for 24 hours at 37° C. in a carbon dioxide incubator, treated with a cathepsin B inhibitor (50 µg/L) and then stabilized for 24 hours. Then, the HT-29 cells were incubated with RR-S-Ac$_3$ManNAz (5 µM) or Ac$_3$ManNAz (5 µM) for 72 hours at 37° C. in a carbon dioxide incubator and the fluorescence of DBCO-Cy5 bound to the expressed azide was observed using a confocal microscope in the same manner as in Example 2.

Figure 5A:
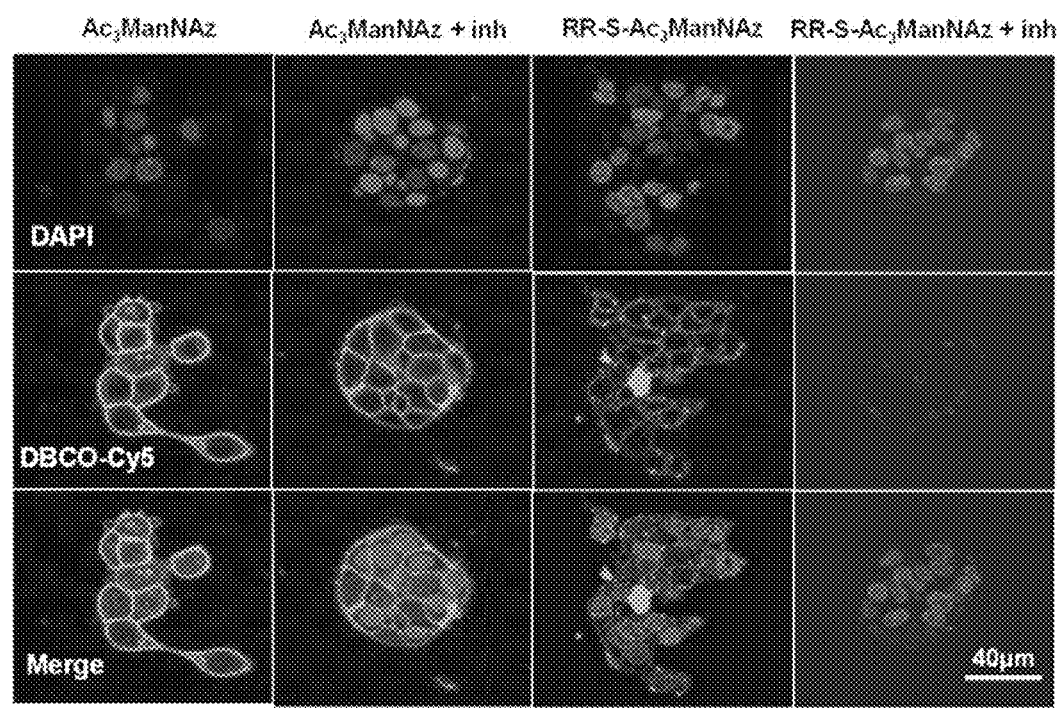
FIG. 5A shows confocal microscopic images for investigating the expression of azide on the surface of HT-29 cells in Example 3.

FIG. 5A shows the confocal microscopic images confirming that the expression of azide on the surface of the HT-29 cells occurs in a cathepsin B-specific manner. The HT-29 cells treated with RR-S-Ac$_3$ManNAz showed significant decrease in the fluorescence intensity by DBCO-Cy5 in the presence of the cathepsin B inhibitor. In contrast, the fluorescence intensity of the Ac$_3$ManNAz-treated HT-29 cells was not affected by the cathepsin B inhibitor.

The incubated cells were treated with trypsin-EDTA and then with 5 µM DBCO-Cy5 for 2 hours. Then, after washing 3 times with DPBS using a centrifuge, the cells were dispersed in DPBS (2% FBS) and analyzed by flow cytometry.

Figure 5B:
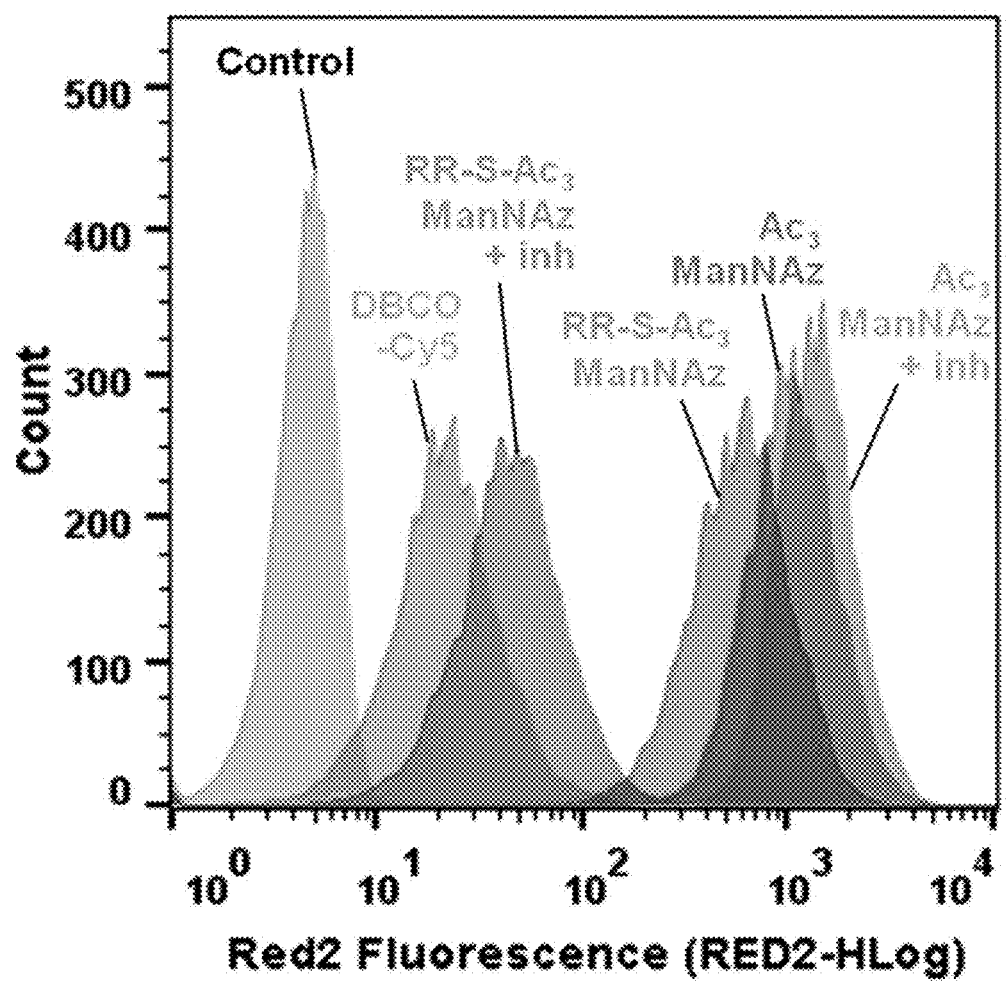
FIG. 5B shows a result of quantifying the fluorescence intensity of DBCO-Cy5 via flow cytometry in Example 3.

As seen from FIG. 5B, the mean fluorescence intensities (MFIs) of the RR-S-Ac$_3$ManNAz-treated HT-29 cells was 10.16-fold higher when the cathepsin B inhibitor was not added than those of the cathepsin B inhibitor-treated cells. In contrast, the Ac$_3$ManNAz-treated HT-29 cells showed no change in fluorescence intensity in the presence of the cathepsin B inhibitor although the shift of peaks could be observed.

The incubated cells were lysed by treating with trypsin-EDTA and then incubated with 500 nM phosphine-PEG-biotin for 6 hours. Each sample was electrophoresed on 10% SDS-PAGE gel at 80 V for 2 hours and 30 minutes and then transferred at 120 V for 1 hour and 30 minutes. After blocking in a blocking solution (BSA 75 mg TBS-T 15 mL) for 1 hour, the sample was incubated with streptavidin-HRP (10000:1) at 4° C. for 24 hours.

Figure 5C:
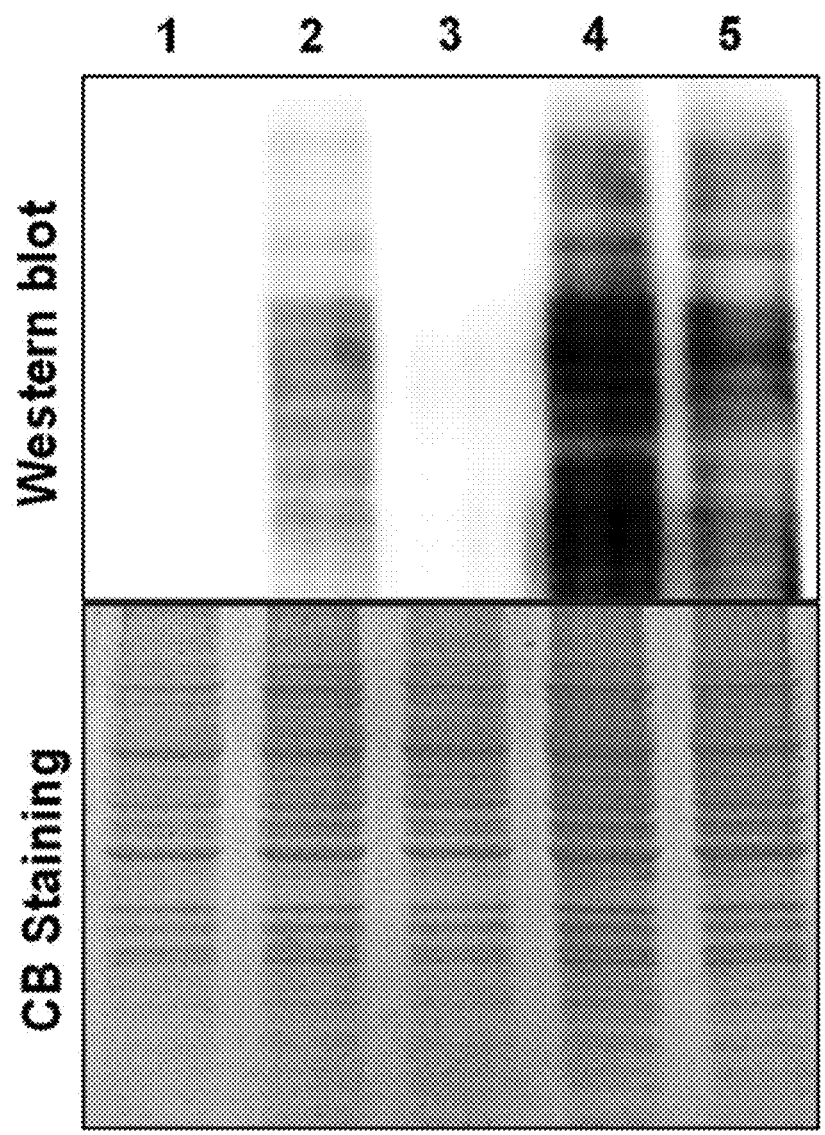
FIG. 5C shows western blot images of test groups in Example 3.

As can be seen from the western blot result of FIG. 5C, the cells treated with RR-S-Ac$_3$ManNAz or Ac$_3$ManNAz showed strong band intensities as compared to the HT-29 cells not treated with RR-S-Ac$_3$ManNAz or Ac$_3$ManNAz. In particular, it was confirmed that the treatment with the cathepsin B inhibitor leads to inhibited expression of the azide reporting monosaccharide from the glycopeptide. This strongly suggests that the azide reporting monosaccharide can be expressed onto the cancer cell surface only when Ac$_3$ManNAz is released by being cleaved from RR-S-Ac$_3$ManNAz by cathepsin B.

Example 4: Evaluation of Azide Expression Efficiency in Normal Cells by RR-S-Ac$_3$ManNAz In order to investigate whether the substrate peptide is cleaved from RR-S-Ac$_3$ManNAz by cathepsin B and azide is expressed onto the cell surface also in normal cells such as human-derived dermal fibroblasts (HDF cells), human-derived umbilical vein endothelial cells (HUVEC cells) and rat cardiomyocytes (H9C2 cells), as in the HT-29 cancer cells, 2.0×10$^4$ HT-29 cells, human-derived dermal fibroblasts (HDF), human-derived umbilical vein endothelial cells (HUVEC) and rat cardiomyocytes (H9C2) were seeded onto 35-mm cover glass bottom dishes and incubated with RR-S-Ac$_3$ManNAz (5 μM) or Ac$_3$ManNAz (5 μM) for 72 hours at 37° C. in a carbon dioxide incubator. Then, the fluorescence of DBCO-Cy5 bound to the expressed azide was observed using a confocal microscope in the same manner as in Example 2.

Figure 6A:
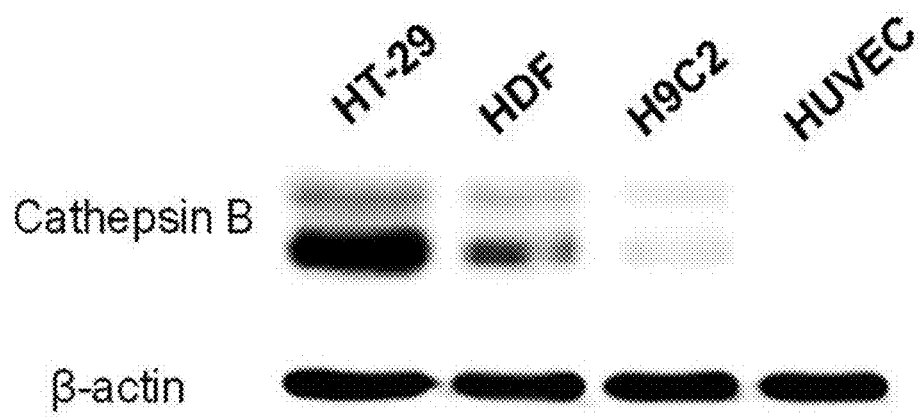
FIG. 6A shows western blot images showing expression of cathepsin B in HT-29 cells, human-derived dermal fibroblasts (HDF cells), human-derived umbilical vein endothelial cells (HUVEC cells) and rat cardiomyocytes (H9C2 cells) in Example 4.
Figure 6B:
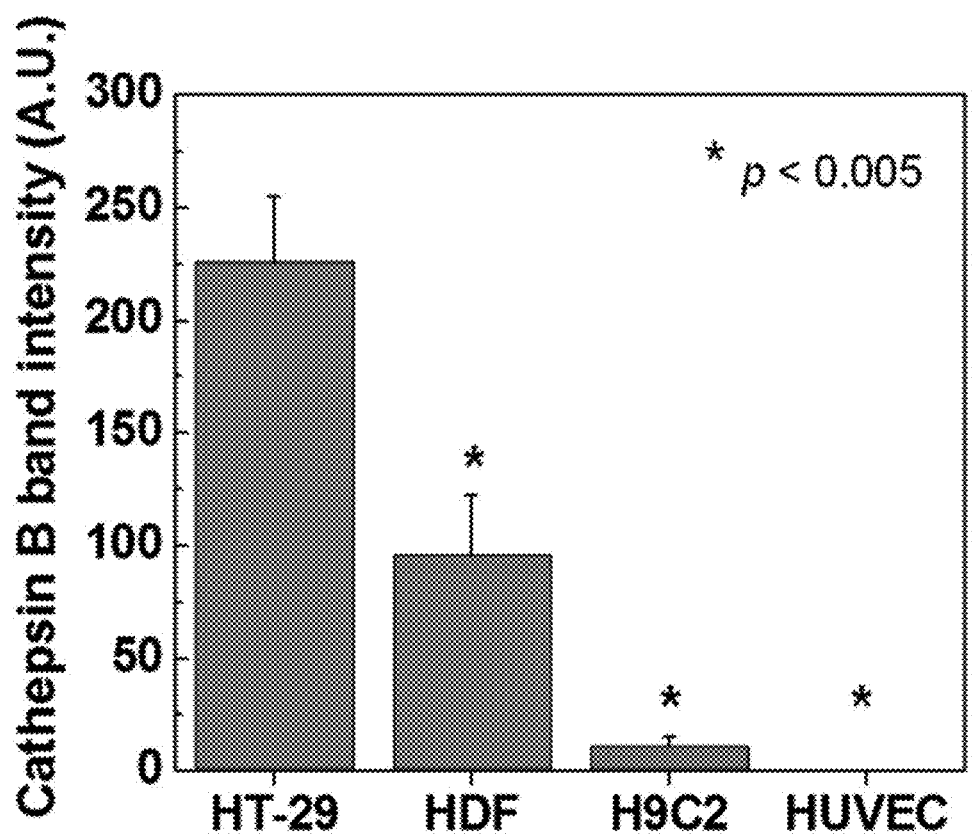
FIG. 6B shows the band intensity of the western blot images of FIG. 6A.

As can be seen from FIG. 6A and FIG. 6B, the cathepsin B expression level was significantly lower in the normal cells such as the HDF cells, the HUVEC cells and the H9C2 cells. The relative band intensity showed that the cathepsin B expression level was 2.3-200 folds higher in the HT-29 cells than those of the normal cells.

Figure 6C:
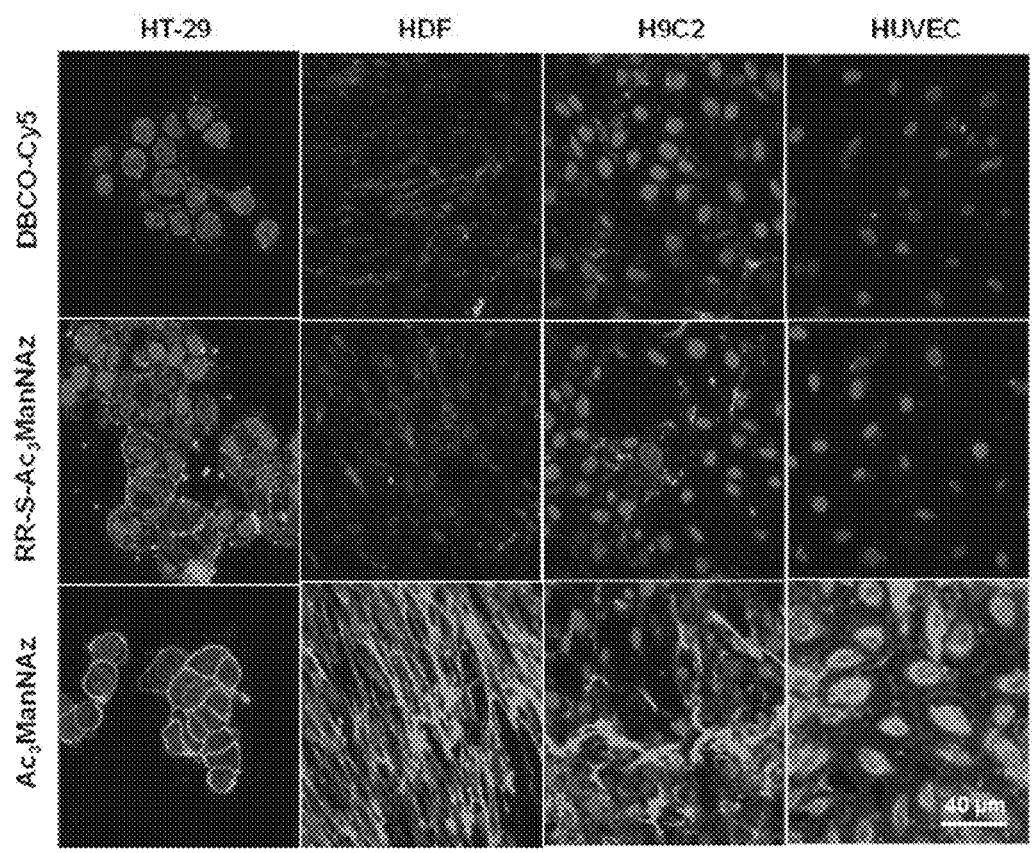
FIG. 6C shows the confocal microscopic images showing expression of azide in test groups in Example 4.

Also, as can be seen from FIG. 6C, although the fluorescence intensity was similar for the normal cells and the cancer cells when they were treated with Ac$_3$ManNAz, azide was expressed only on the surface of the HT-29 cells when they were treated with RR-S-Ac$_3$ManNAz.

Example 5: Expression of Azide in Cancer Tissue Via Intratumoral Injection of RR-S-Ac$_3$ManNAz in Tumor-Bearing Animal Model To prepare a tumor-bearing animal model, 1×10$^7$ HT-29 cells were injected into both flanks of 5-week-old male nude mice. When tumors grew to 200-250 mm$^3$ in volume after 5 weeks, 2 mg/kg of a cathepsin B inhibitor (Z-Phe-Ala fluoromethyl ketone, CAS 197855-65-5) administered 4 times into the left cancer tissue of the tumor-bearing animal model via intratumoral injection 24 hours before treatment with RR-S-Ac$_3$ManNAz. Then, 4 mg/kg of RR-S-Ac$_3$ManNAz was intratumorally into tumors of both sides for 4 days. To observe azide expressed in the cancer tissue, 100 μg of azadibenzocyclooctyne-Cy5.5 (DBCO-Cy5.5) (200 μL) was administered intravenously and near-infrared fluorescence imaging was conducted 24 hours later. Then, major organs were excised and fluorescence from the organs was detected.

In order to observe the fluorescence from the cancer tissue, frozen sections of the cancer tissue were prepared and observed using a confocal microscope.

FIGS. 7A to 7E show the near-infrared fluorescence image of azide in the HT-29 tumor-bearing animal model, the fluorescence images of major organs obtained using a confocal microscope, the result of quantifying the azide expression in the cancer tissue, the fluorescence images of the cancer tissue and the result of western blot analysis.

Figure 7A:
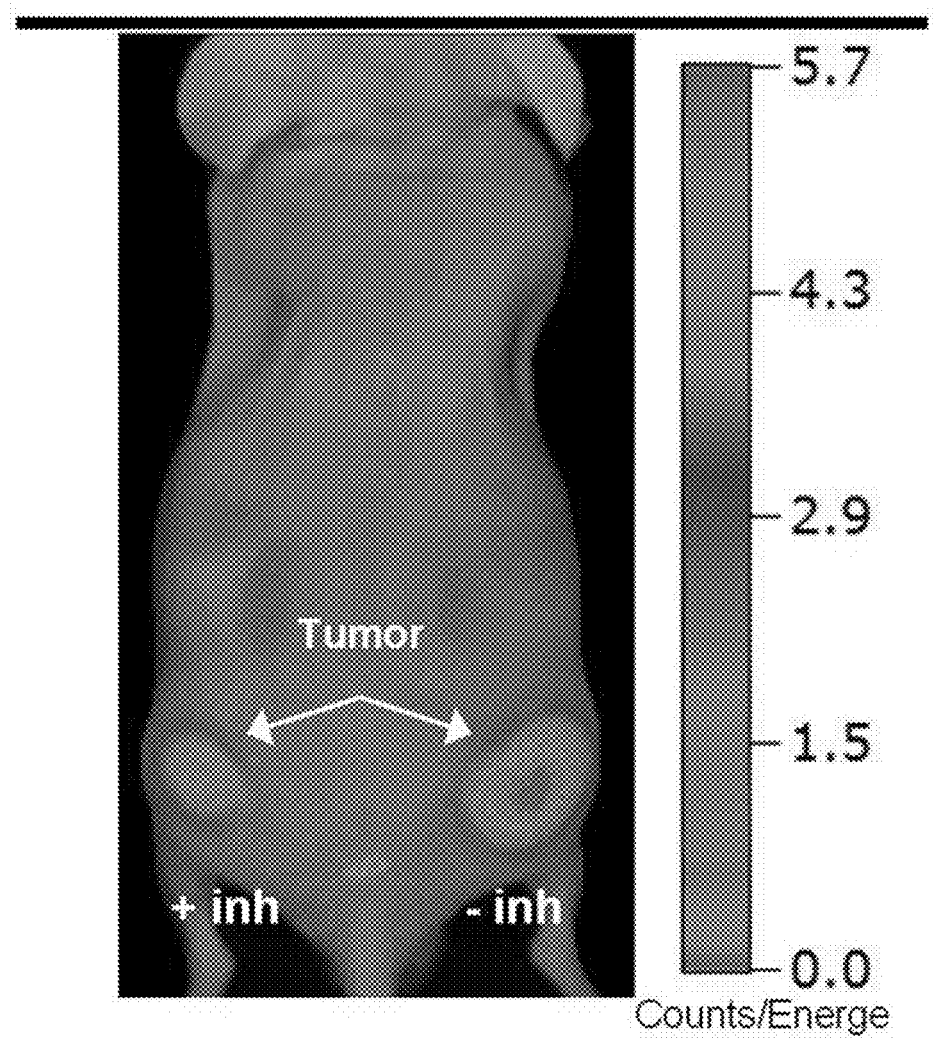
FIG. 7A shows a near-infrared fluorescence image for targeting azide in cancer tissue into which RR-S-Ac$_3$ManNAz is injected directly in an HT-29 tumor-bearing animal model in Example 5.

As can be seen from FIG. 7A, the tumor-bearing animal model showed significant difference in the fluorescence intensity in the left and right flanks. RR-S-Ac$_3$ManNAz could effectively detect cancer not only in the cell level but also in the tumor-bearing animal model by targeting the azide.

Figure 7B:
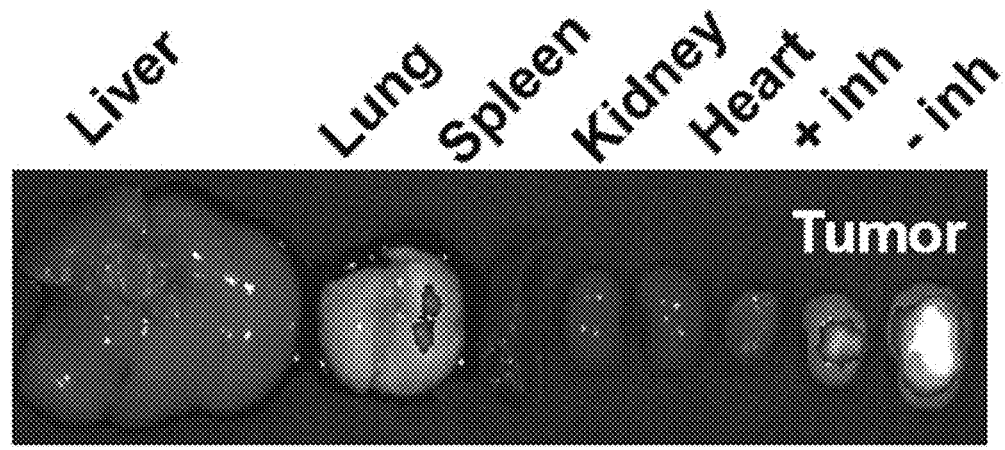
FIG. 7B shows the near-infrared fluorescence images of major organs in Example 5.

It was also confirmed that the fluorescence intensity of the left and right flanks of FIG. 7A was higher than that of the major organs of FIG. 7B. This suggests that RR-S-Ac$_3$ManNAz generates the azide reporting monosaccharide on the surface of the cancer tissue and the azide reporting monosaccharide is chemically labeled with DBCO-Cy5.5 via a bioorthogonal click reaction.

Figure 7C:
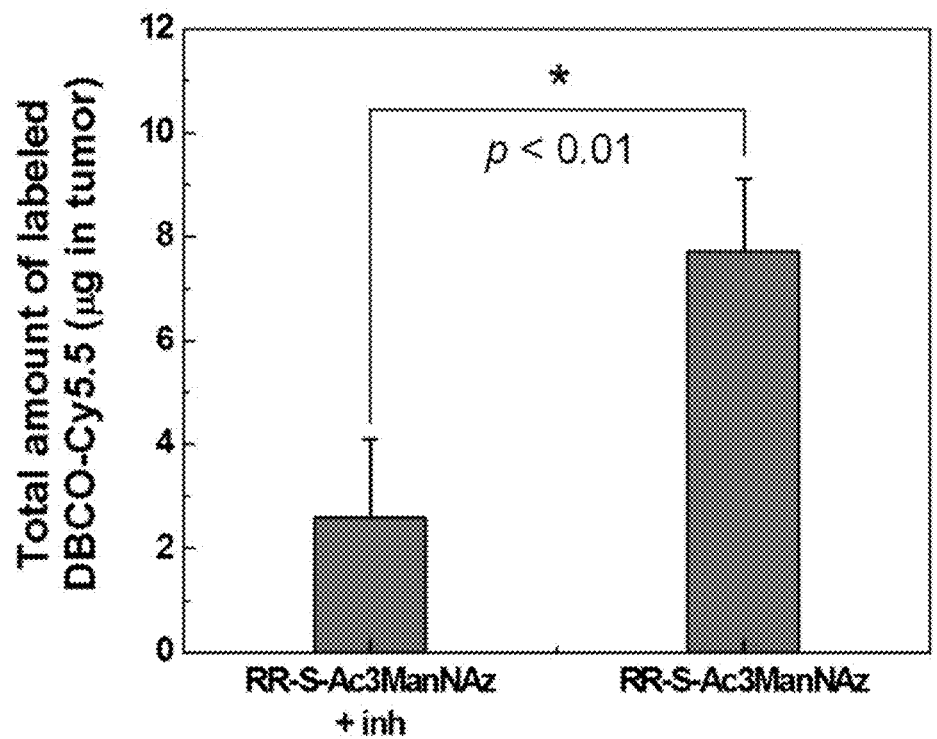
FIG. 7C shows a result of quantifying the fluorescence intensity in the image of FIG. 7A.

For more precise analysis, fluorescence molecular topography was conducted for the cancer tissue and the result is shown in FIG. 7C. The fluorescence intensity of DBCO-Cy5.5 in the right cancer tissue was 2.97 folds higher than the left cancer tissue.

Figure 7D:
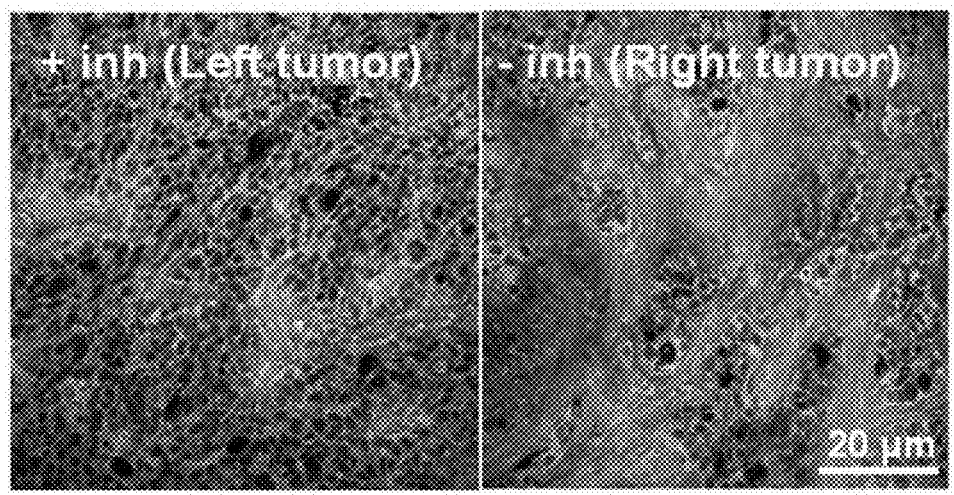
FIG. 7D shows a result of immunofluorescence staining cathepsin B and azide present in cancer tissue in Example 5.

In addition, the right cancer tissue treated with RR-S-Ac$_3$ManNAz showed stronger red fluorescence of DBCO-Cy5.5 than the left cancer tissue treated with the cathepsin B inhibitor and RR-S-Ac$_3$ManNAz (see FIG. 7D). This suggests that the azide reporting monosaccharide was not generated on the surface of the left cancer tissue due to the cathepsin B inhibitor.

Figure 7E:
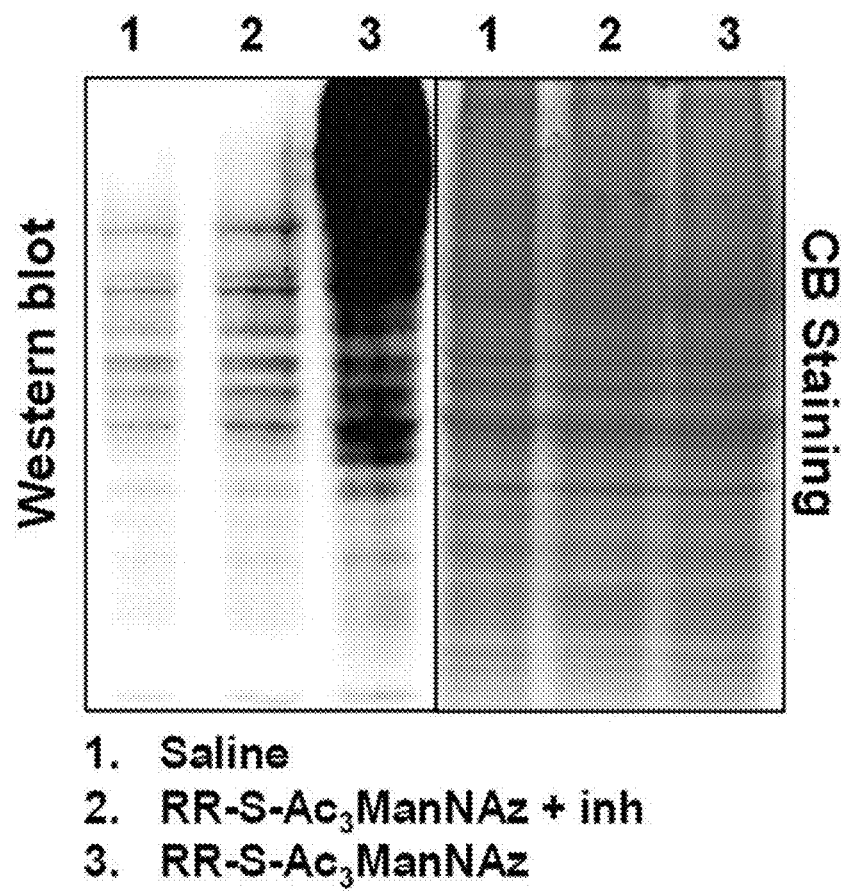
FIG. 7E shows a result of quantifying an azide reporting monosaccharide produced on the surface of HT-29 cancer tissue via western blot. Coomassie staining visualizes the total amount of proteins.

A result of analyzing the amount of the azide reporting monosaccharide via western blot to quantify the azide groups generated on the surface of the HT-29 cancer tissue is shown in FIG. 7E. A significantly stronger band intensity could be confirmed when RR-S-Ac$_3$ManNAz was injected into the cancer tissue as compared to when physiological saline or the cathepsin B inhibitor was injected.

Example 6: Expression of Azide in Cancer Tissue Via Intravenous Injection of RR-S-Ac$_3$ManNAz in Tumor-Bearing Animal Model To prepare a tumor-bearing animal model, 1×10$^7$ HT-29 cells were injected into the left flank of 5-week-old male nude mice. When tumors grew to 200-250 mm$^3$ in volume after 5 weeks, 32 mg/kg of RR-S-Ac$_3$ManNAz was injected into the tail vein of the tumor-bearing animal model for 3 days. In order to target the azide expressed in the cancer tissue, 100 μg of azadibenzocyclooctyne-Cy5.5 (DBCO-Cy5.5) (200 μL) was injected intravenously and near-infrared fluorescence imaging was conducted 24 hours later.

Figure 8A:
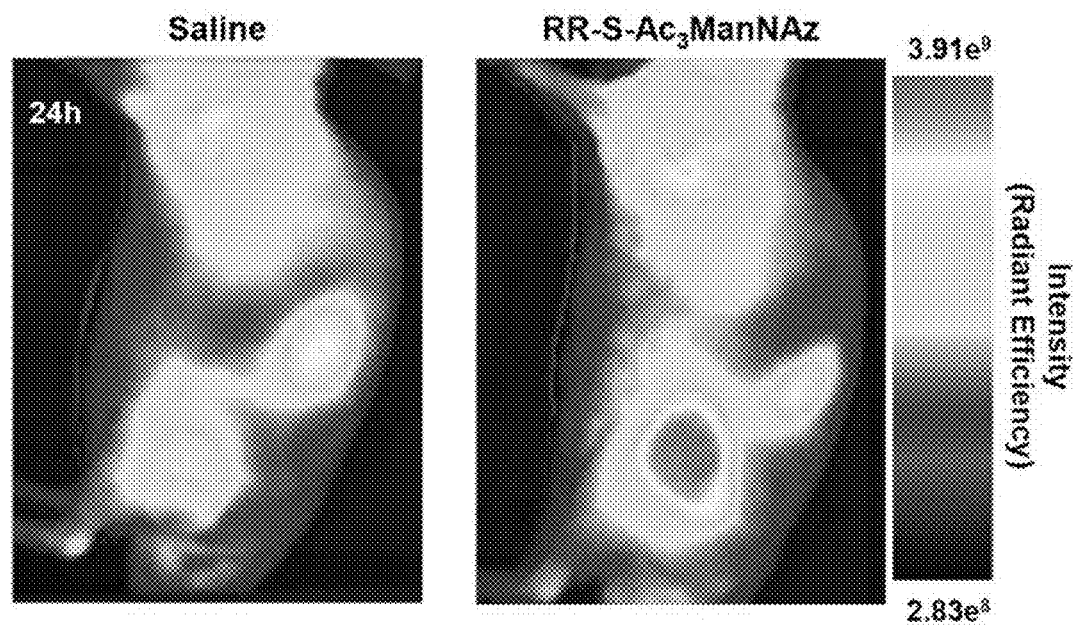
FIG. 8A shows near-infrared fluorescence images for targeting azide in an HT-29 tumor-bearing animal model via intravenous injection of RR-S-Ac$_3$ManNAz in Example 6.

As can be seen from FIG. 8A, a significant difference in fluorescence intensity was observed in the left flank of the tumor-bearing animal model. Accordingly, it was confirmed that RR-S-Ac$_3$ManNAz can express azide specifically in cancer tissue when it is injected intravenously, as well as intratumorally, and cancer can be effectively detected by targeting the azide expressed in the cancer tissue.

Figure 8B:
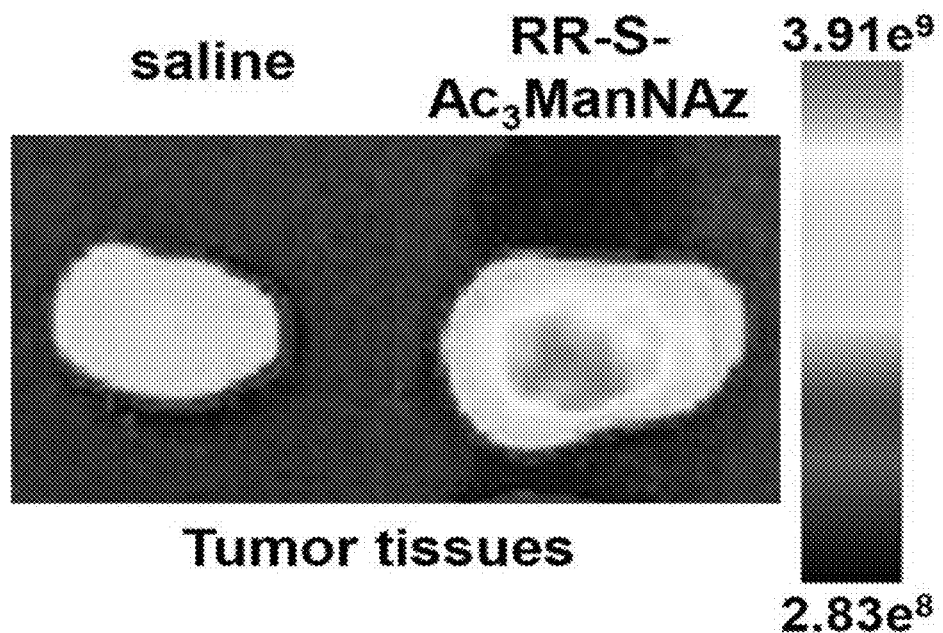
FIG. 8B shows fluorescence images showing expression of azide in cancer tissue in Example 6.
Figure 8C:
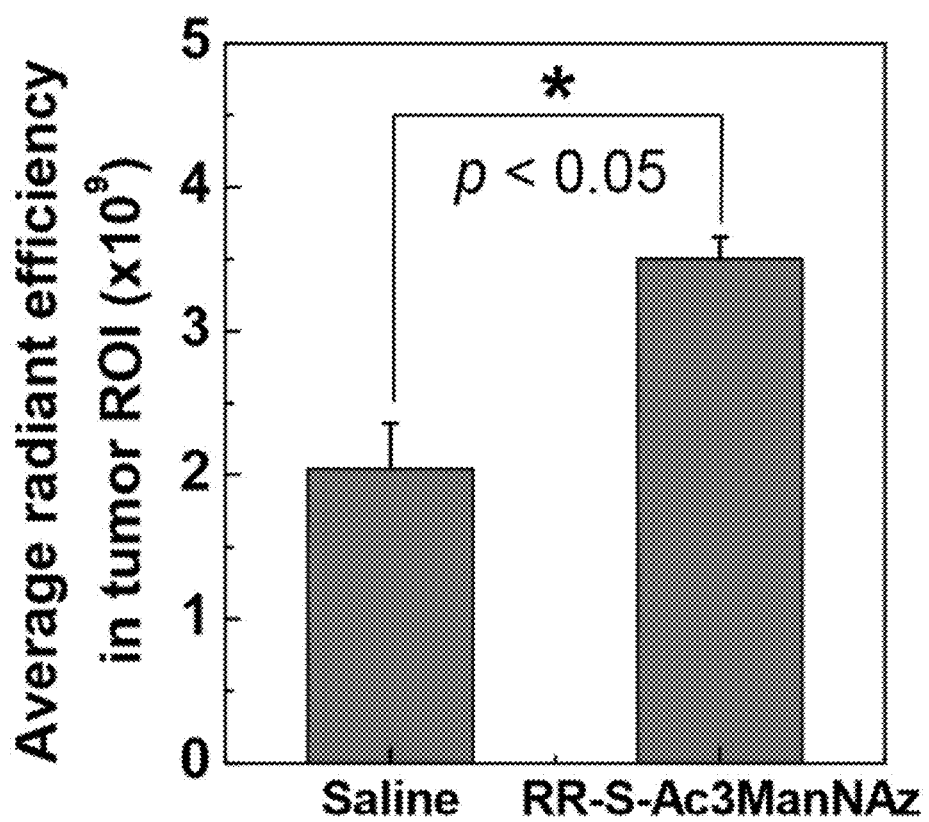
FIG. 8C shows the fluorescence intensity of the image of FIG. 8B.

Also, as can be seen from FIG. 8B and FIG. 8C, it was confirmed that the fluorescence intensity was higher also in the cancer tissue of the animals to which RR-S-Ac$_3$ManNAz was injected intravenously. This suggests that RR-S-Ac$_3$ManNAz generates an azide reporting monosaccharide on the cancer tissue and the azide reporting monosaccharide is chemically labeled with DBCO-Cy5.5 via a bioorthogonal click reaction.

What is claimed is:

1. A glycopeptide for a contrast agent targeting cancer cells, comprising:
   an azide reporting monosaccharide; and
   a substrate peptide, wherein
   the azide reporting monosaccharide and the substrate peptide are bound to form the glycopeptide,
   the azide reporting monosaccharide is selected from N-azidoalkyl-D-mannosamine, N-azidoalkyl-D-galactosamine and N-azidoalkyl-D-glucosamine,
   the substrate peptide has 4-30 amino acids and an amino acid sequence of SEQ ID NO: 1, and
   the substrate peptide is specifically cleavable by cathepsin B in a cancer cell.

2. The glycopeptide according to claim 1, further comprising: a linker, wherein the linker is bound between the substrate peptide and the azide reporting monosaccharide.

3. The glycopeptide according to claim 1, wherein the alkyl in N-azidoalkyl-D-mannosamine, N-azidoalkyl-D-galactosamine and N-azidoalkyl-D-glucosamine is $C_1$-$C_3$ alkyl.

4. The glycopeptide according to claim 2, wherein the linker is selected from 6-maleimidocaproyl (MC), maleimidopropanoyl (MP), valine-citrulline (val-cit), alanine-phenylalanine (ala-phe), p-aminobenzyloxycarbonyl (PAB), N-succinimidyl 4-(2-pyridylthio)pentanoate (SPP), N-succinimidyl 4-(N-maleimidomethyl)cyclohexane-1 carboxylate (SMCC) and N-succinimidyl (4-iodo-acetyl)aminobenzoate (SIAB).

5. A contrast agent kit targeting cancer cells, comprising: the glycopeptide according to claim 1; and a cyclooctyne-labeling fluorescent material.

6. The contrast agent kit targeting cancer cells according to claim 5, wherein the cyclooctyne is selected from a group consisting of dibenzylcyclooctyne (DBCO), difluorocyclooctyne (DIFO), bicyclononyne (BCN), dibenzoazacyclooctyne (DIBAC), dibenzocyclooctynol (DIBO) and azadibenzocyclooctyne (ADIBO).

7. A contrast agent kit targeting cancer cells, comprising: the glycopeptide according to claim 2; and a cyclooctyne-labeling fluorescent material.

8. A contrast agent kit targeting cancer cells, comprising: the glycopeptide according to claim 3; and a cyclooctyne-labeling fluorescent material.

9. A contrast agent kit targeting cancer cells, comprising: the glycopeptide according to claim 4; and a cyclooctyne-labeling fluorescent material.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Substrate peptide for cathepsin B

<400> SEQUENCE: 1

Lys Gly Arg Arg
 1
```